US008868716B2

(12) United States Patent  
Muralidharan

(10) Patent No.: US 8,868,716 B2  
(45) Date of Patent: Oct. 21, 2014

(54) METHOD AND APPARATUS FOR DYNAMICALLY ADAPTING IMAGE UPDATES BASED ON NETWORK PERFORMANCE

(75) Inventor: Girish K. Muralidharan, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 3431 days.

(21) Appl. No.: 10/723,864

(22) Filed: Nov. 26, 2003

(65) Prior Publication Data

US 2005/0114395 A1 May 26, 2005

(51) Int. Cl.
*G06F 15/173* (2006.01)
*G06F 19/00* (2011.01)

(52) U.S. Cl.
CPC .................................. *G06F 19/321* (2013.01)
USPC ........................................ 709/224; 709/225

(58) Field of Classification Search
USPC ......................................................... 709/235
See application file for complete search history.

(56) References Cited

U.S. PATENT DOCUMENTS

| | | | | |
|---|---|---|---|---|
| 5,119,319 | A * | 6/1992 | Tanenbaum | 709/205 |
| 5,851,186 | A * | 12/1998 | Wood et al. | 600/437 |
| 5,968,132 | A * | 10/1999 | Tokunaga et al. | 709/247 |
| 6,642,943 | B1 * | 11/2003 | Machida | 715/763 |
| 7,047,312 | B1 * | 5/2006 | Aweya et al. | 709/235 |
| 7,133,915 | B2 * | 11/2006 | Benejam et al. | 709/224 |
| 7,143,159 | B1 * | 11/2006 | Grace et al. | 709/224 |
| 2002/0018587 | A1 * | 2/2002 | Ueda | 382/128 |
| 2002/0029285 | A1 * | 3/2002 | Collins | 709/232 |
| 2002/0082864 | A1 * | 6/2002 | Kelley et al. | 705/2 |
| 2002/0087716 | A1 * | 7/2002 | Mustafa | 709/236 |
| 2004/0005094 | A1 * | 1/2004 | Huffman | 382/232 |
| 2004/0054667 | A1 * | 3/2004 | Kake et al. | 707/3 |
| 2004/0138754 | A1 * | 7/2004 | Lang et al. | 623/20.14 |
| 2004/0165538 | A1 * | 8/2004 | Swami | 370/252 |
| 2005/0023356 | A1 * | 2/2005 | Wiklof et al. | 235/462.42 |
| 2005/0111711 | A1 * | 5/2005 | Deaven et al. | 382/128 |

OTHER PUBLICATIONS

'Company in the Spotlight: UPMC-inspired Stentor to challenge in medical imaging', Pamela Gaynor, post-gazette.com, Jul. 9, 2000.*
'Stentor: Just what the doctor ordered', Jason Meserve, Network World, Nov. 12, 2001.*
'PAC Pays (Really)', Lin Muschlitz, Technology Management, Feb. 2000.*
'A Practical Discrete Multitone Transceiver Loading Algorithm for Data Transmission over Spectrally Shaped Channels', Peter Chow, John Cioffi, John Bingham, IEEE Transactions on Communications, vol. 43, No. 2/3/4, Feb./Mar./Apr. 1995.*

* cited by examiner

*Primary Examiner* — Karen Tang
(74) *Attorney, Agent, or Firm* — Fletcher Yoder, P.C.

(57) ABSTRACT

A technique is provided for dynamically adjusting information transmitted between a served station and a serving station. In the present technique, an imaging system may be configured to detect and convert signals into an image. Also, the imaging system may be configured to produce image data. A serving station is configured to receive the image data from the imaging system along with network performance data from network sensors. The serving station has a scanner module configured to dynamically modify a scanning rate of the image data based on the network performance. Similarly, the serving station has an encoder module configured to dynamically modify an encoding format of the image data based on the network performance. A served station is configured to receive the modified image data from the serving station via a network.

37 Claims, 4 Drawing Sheets

METHOD AND APPARATUS FOR DYNAMICALLY ADAPTING IMAGE UPDATES BASED ON NETWORK PERFORMANCE

BACKGROUND OF THE INVENTION

The present invention relates generally to the remote configuration and observation of an imaging system over a network. More specifically, the present invention relates to a technique for dynamically adapting the image updates for a remote console observation based on network performance.

Medical institutions and facilities offer an increasingly wide range of services and procedures to address the needs of the patients. The services offered by the medical institutions, such as hospitals, clinics, and other medical facilities, may include medical imaging of the patients. A wide variety of medical imaging systems, such as x-ray system, computed tomography (CT) system, positron emission tomography (PET) system, electron beam tomography (EBT) system, magnetic resonance imaging (MRI) system, ultrasound system, tomosynthesis system, and so forth may be utilized in the medical facilities. The medical imaging systems may produce detailed images of a patient's internal tissues and organs, thereby mitigating the need for invasive exploratory procedures and providing valuable tools for identifying and diagnosing disease or for verifying wellness.

To provide support for the medical imaging systems, technicians and other support personnel may be utilized to train personnel on the operation of the medical imaging systems and/or to troubleshoot problems with the medical imaging systems. Though the number of these imaging systems has increased, the personnel qualified to service the imaging systems or assist in instructing new technicians in their use has not increased at the same rate. In addition, because the medical imaging systems may be geographically dispersed, the support of these imaging systems may be very costly. It may not be feasible for a technician to travel to each medical imaging system to provide the training and/or the troubleshooting needed.

To address the cost and support issues, the instructors and/or the technicians may remotely interact with the local operator workstation through a remote console observation to provide training and/or troubleshooting for the imaging system. The remote console observation may utilize a network that connects the local operator workstation at the imaging system with the remote operator workstation to provide the interaction between the systems. By utilizing the network for this interaction, travel time and costs associated with the servicing and training of personnel for the medical imaging systems may be reduced. For example, a remote service technician may access the imaging system to perform diagnostic routines, to configure imaging settings, or to train a local operator of the imaging system, while being located in a centralized service center.

Typically, updates of screen information may be transmitted to the local operator's workstation and the remote operator's workstation to display images from the imaging system. The remote operator and the local operator may also provide inputs, such as mouse movements or text, which are displayed on the respective workstations. However, the screen updates for the remote operator workstation are directly impacted by the performance of the network. For instance, as network congestion increases, the latency of the network may also increase. These network performance problems may delay the screen updates received at the remote operator workstation. As a result, the updates may be sporadic or slowed down based on the congestion or bandwidth problems being experienced on the network. The operator at the imaging system or the remote workstation may be unaware of the cause of the deterioration in the quality of the remote console observation. Accordingly, the network performance may hinder the interaction of the operators in the remote console observation.

To adjust for these conditions, the operator at the imaging system may have to manually adjust the screen capture rate or the amount of data being placed on the network. Because the network may be subject to various fluctuations, the operator at the imaging system may have to adjust the screen capture rate numerous times during a training session or while diagnosing or otherwise addressing a problem. With each time the system has to be manually adjusted, the portions of the imaging system may have to be restarted to incorporate the adjustments. Accordingly, the manual adjustment to account for network performance hinders the training or the diagnostics process. It is therefore desirable to allow remote servicing and training to be performed on a medical imaging system, which dynamically adapts the image updates for a remote operator workstation based on network performance, such as network congestion or latency.

BRIEF DESCRIPTION OF THE INVENTION

The present invention relates generally to dynamically adapting the remote console observation between remote service engineers and/or instructors and local operators to account for network performance when operating remotely with a medical imaging system. In particular, the technique provides for adjusting imaging parameters, such as compression and scanning rate, based on network performance without user intervention. In addition, the remote service engineers and/or instructors and local operators may receive an indication of the network performance during the operation of the imaging system for the remote console observation. In this manner, the remote console observation may account for network performance and notify the personnel involved in the remote console observation about the network performance.

In accordance with one aspect of the present technique, a method and system for dynamically adapting image updates based on network performance are provided. The system may convert imaging data from an imaging modality into screen updates. The system may also measure the performance of a network between a local operator workstation and a remote operator workstation. Based on the measured network performance, the system may adjust the screen updates that are transmitted to a remote operator workstation, which may be made without the intervention of the local operator. The modified screen updates may be displayed at the remote operator workstation for viewing by a remote operator. In addition, an indication of the network performance may be displayed at the local operator workstation and/or the remote operator workstation to notify the operator of network performance.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
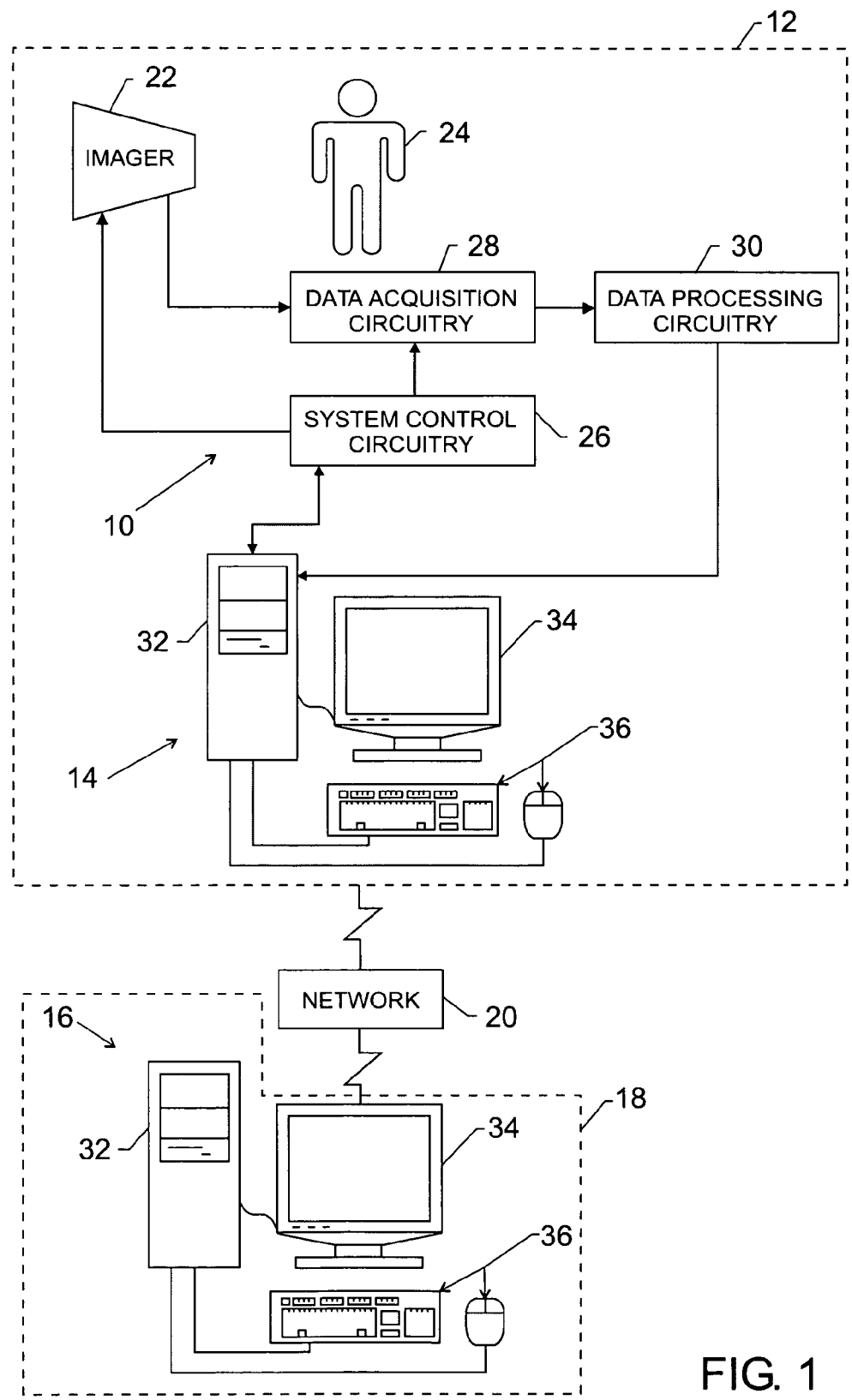
FIG. 1 is a general diagrammatical representation of certain functional components of an exemplary medical imaging system configured for remote operation via the present technique.

Turning now to the drawings, referring initially to FIG. 1, an exemplary medical imaging system 10 is depicted. Such imaging systems are typically complex and require periodic maintenance of the imaging system 10 and/or periodic instruction for technicians or personnel using the imaging system 10. As the availability of qualified service technicians may be limited, remote access for training and diagnostics purposes may be utilized. The imaging system 10 may be located in a variety of geographically disperse locations, such as a medical facility 12, which may increase travel costs and time associated with providing service to the imaging system 10. Accordingly, it may be desirable to provide remote access for training and diagnostic purposes to limit the travel costs associated with the training and diagnostic servicing of the medical imaging system 10.

To remotely observe a serving station, such as a local operator workstation 14 that is connected to the imaging system 10, a served station, such as a remote operator workstation 16 at a service provider 18, may utilize a network 20 to interact with the imaging system 10. The performance of the network 20 may impact the remote observation of the local operator workstation 14. Because the network 20 is outside the control of the imaging system's operator or technician, it may be desirable to adjust the image updates transmitted to the remote operator workstation 16 based on congestion or latency on the network 20. In making these adjustments, it may further be advantageous to dynamically or automatically adjust the interaction based on the network performance without manual intervention by the operator. In this manner, the remote observation between the local operator workstation 14 at imaging system 10 and the remote operator workstation 16 may be able to compensate for network performance.

The imaging system 10 is located within the medical facility 12. The medical facility 12 may include a single location, a site, or multiple sites, which may be geographically dispersed. Generally, the imaging system 10 includes an imager 22 that detects signals and converts the signals into useful data. As described more fully below, the imager 22 may operate in accordance with various physical principals for creating the image data. The imager 22 creates image data indicative of regions of interest in a patient 24, either in a conventional film or in a digital media.

The imager 22 operates under the control of system control circuitry 26. The system control circuitry 26 may include a wide variety of circuits, such as radiation source control circuits, timing circuits, circuits for the coordination of data acquisition in conjunction with patient or table movement, circuits for controlling the position of the radiation source and detectors and so forth. In the present context, the system control circuitry 26 may also include memory elements for storing programs and routines executed by the system control circuitry 26 or by associated components of the imaging system 10.

The imager 22, following acquisition of the image data or signals, may process the signals, such as for conversion to digital values, and forward the image data to data acquisition circuitry 28. In the case of analog media, such as photographic film, the data acquisition system may generally include supports for the film, as well as equipment for developing the film and producing hard copies that may be subsequently digitized. For digital systems, the data acquisition circuitry 28 may perform a wide range of initial processing functions, such as adjustment of digital dynamic ranges, smoothing or sharpening of data, as well as compiling of data streams and files, where desired. The data may then be transferred to data processing circuitry 30 where additional processing and analysis are performed. For conventional media such as photographic film, the data processing system may apply textual information to films, as well as attach certain notes or patient-identifying information. For the various digital imaging systems available, the data processing circuitry 30 perform substantial analyses of data, ordering of data, sharpening, smoothing, feature recognition, and so forth. The acquired images or image data may be stored in short or long-term storage devices, such as picture archiving communication systems, which may be comprised within or remote from the imaging system 10.

The above-described operations and functions of the imaging system 10 may be controlled by a local operator workstation 14, which typically interfaces with the system control circuitry 26. The local operator workstation 14 may include one or more general purpose or application specific computers 32 or processor-based components. The local operator workstation 14 may include a monitor 34 or other visual display and one or more input devices 36. The monitor 34 and input devices 36 may be used for viewing and inputting configuration information or for operating the imaging system 10, in accordance with the techniques discussed herein. As with the system control circuitry 26, the local operator workstation 14 may communicate with a memory or data storage component for storing programs and routines executed by the local operator workstation 14 or by associated components of the imaging system 10. It should be understood that any type of computer accessible memory or storage device capable of storing the desired amount of data and/or code may be accessed by the local operator workstation 14. Moreover, the memory or storage device may comprise one or more memory devices, such as magnetic or optical devices, of similar or different types, which may be local and/or remote to the imaging system 10.

It should be noted that a serving station, such as the local operator workstation 14, may be a laptop, a workstation, a server, or any other suitable device that may receive image data and transmit the image data to a served station, such as the remote operator workstation 14. Also, it should be noted that more than a single local operator workstation 14 may be provided. For example, an imaging scanner or station may include an interface which permits regulation of the parameters involved in the image data acquisition procedure, whereas a different operator interface may be provided for manipulating, enhancing, and viewing the reconstructed images.

In addition, a remote operator workstation 16 may communicate with the imaging system 10, such as via a network 20. The network 20 may include a local area network (LAN), storage area network (SAN), a wide area network (WAN), or a metropolitan area network (MAN), or may even provide network connectivity through the Internet. For instance, the network 20 may include a local intranet within the medical facility 12, a service network between the medical facility 12 and the service provider 18, a direct communication line between the imaging system 10 and the remote operator workstation 16, a virtual private network (VPN) established over the Internet, and so forth. In general, the network 20 allows data exchange between the remote operator workstation 16 and one or more components of the imaging system 10. As will be appreciated by those skilled in the art, any suitable circuitry, such as modems, routers, switches, servers, firewalls, and so forth may be included within the network 20.

The remote operator workstation 16 may be located in or associated with the service provider 18. The service provider 18 may include a facility or facilities for providing training and technical assistance based on a subscription or contract basis. The remote operator workstation 16 comprises many of the components of the local operator workstation 14, such as a monitor 34 and input devices 36. The remote operator workstation 16 allows a remote operator to access elements of the imaging system 10 via the network 20. In particular, the remote operator workstation 16 may allow a remote operator to configure parameters associated with a scanning operation, access or initiate service operations, configure the processing of acquired scan data, and so forth. It should be noted that the remote operator workstation 16, or other served stations may be a laptop, a workstation, a server, or any other suitable device that may receive data from the serving station, such as the local operator workstation 14.

To remotely observe the imaging system 10 from the remote operator workstation 16, the screen update data may be transmitted from the local operator workstation 14 or the imaging system 10 to the remote operator workstation 16. The remote operator workstation 16 may receive the screen update data and display the images and information through the monitor 34. The screen update data may include screen information that is utilized to display information and detailed images of a patient's anatomy, such as internal tissues and organs. The workstations 14 and 16 may utilize remote frame buffer (RFB) protocol, X windows protocol, independent computing architecture (ICA) protocol, or other similar protocol to communicate the screen updates. The protocols may be an implementation of virtual network computing or other similar software to provide for remote training or diagnostics.

The performance of the network 20 may impact the operation of the remote observation at the remote operator workstation 16. For instance, the network 20 may be congested during certain periods of time during the day. During the peak times of network utilization, the screen update data received at the remote operator workstation 16 may be sporadic or inconsistent because of the network congestion. As a result, the remote operator workstation 16 may lag behind the local operator workstation 14. This lag is associated with the latency of the network 20, which may make the remote observation unusable. In addition, under certain instances of network congestion, the network performance may make the images presented on the monitor 34 of the remote operator workstation 16 appear to be jerky and/or unstable. As a result, it may be desirable to modify the screen update data to account for the network congestion.

Typically, static methods for adapting the imaging system for network congestion have been utilized. These methods include manually changing compression settings or adjusting the scanning rate, which may require restarting the imaging system 10 or local operator workstation 14. The manual adjustment of the imaging system 10 is not effective because the operator at the imaging system 10 has to manually adjust the system to compensate for the network congestion, which may change rapidly and is inconsistent. As a result, the operator of the local operator workstation 14 is not able to adjust the screen update data in a manner to effectively compensate for the network 20 fluctuations. Thus, the remote observation of the imaging system 10 does not perform in an efficient or effective manner. Accordingly, it may be desirable to dynamically measure and adjust the screen update data to compensate for the network performance.

Because the performance of the network 20 may be impacted by network congestion or other factors outside the control or knowledge of the operators, it may be desirable to dynamically or automatically adapt the screen updates received by the remote operator at the remote operator workstation 16. Also, it may be desirable to indicate the condition of the network to the operator of the local operator workstation 14 and/or the remote operator workstation 16 so the operator's expectations may be adjusted. In particular, network sensors may be used by the workstations 14 and 16 to determine network performance and dynamically adapt parameters, such as the frame buffer scanning algorithm or the data transmission algorithm to account for network congestion. The use of the network sensors to modify the screen update data is shown in greater detail in FIG. 2.

Figure 2:
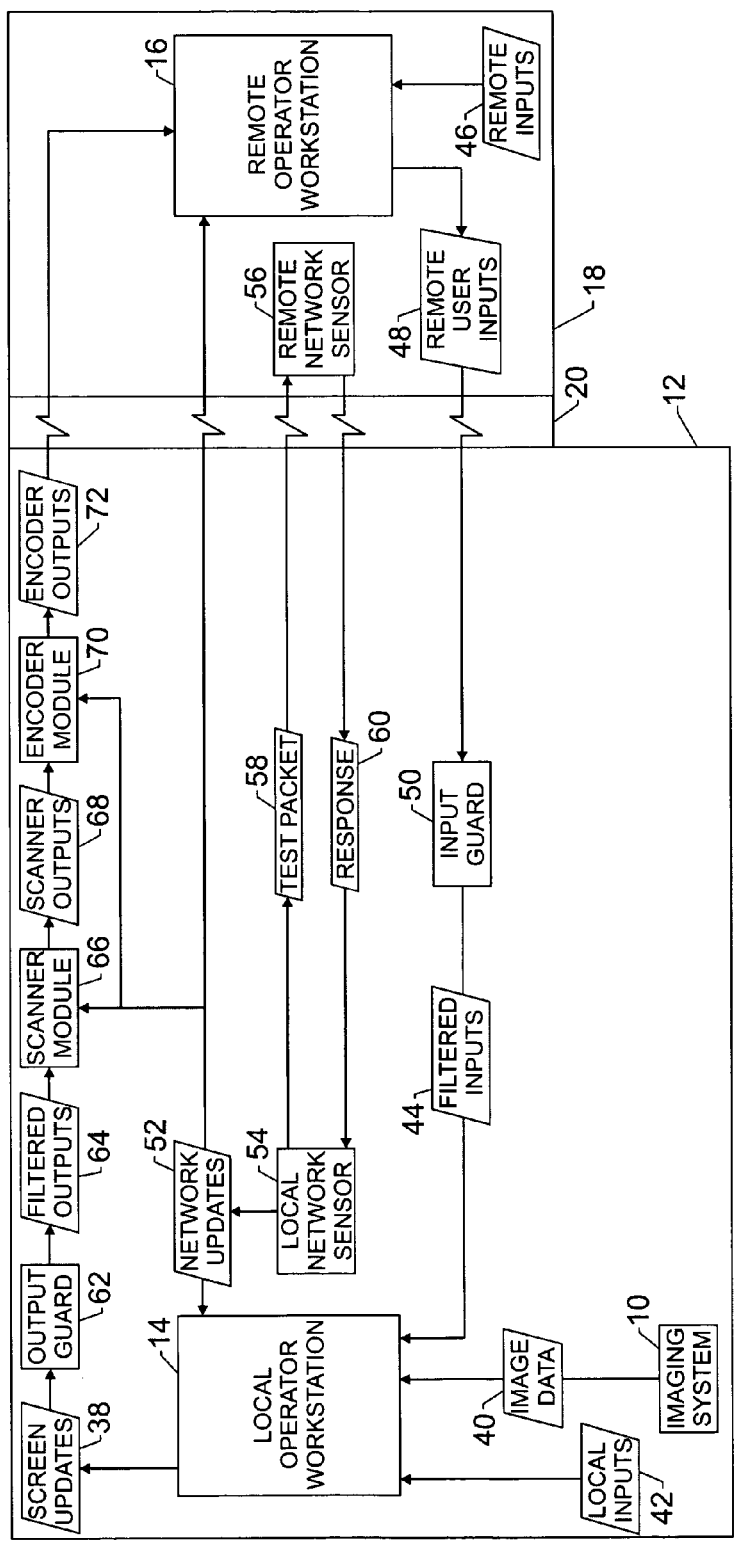
FIG. 2 is block diagram depicting various components of a network monitoring system in accordance with the present technique.

As shown in FIG. 2, the local operator workstation 14 may communicate screen updates 38 to the remote operator workstation 16 via the network 20, as discussed above. The local operator workstation 14 provides the screen updates 38 to the operator of the local operator workstation 14. The screen updates 38 may include screen information that is utilized to display information and images. The images may include a complete image or updates from previous screen images of a patient's anatomy, which may include internal tissues and organs. The information may include updates on the patient name, region, network performance, or other suitable information, as discussed below.

The screen updates 38 may be based on a variety of inputs from the local operator and the imaging system 10. These inputs may be utilized to produce a displayed image on the local operator workstation 14. For instance, one input that may be utilized in the screen updates 38 is image data 40 from the imaging system 10. The imaging system 10 may provide image data 40 that is used to update the images presented on the local operator workstation 14. The image data 40 may include scanned images or patient anatomy regions from the imaging system 10. Another source of input may be the local inputs 42 from the operator of the local operator workstation 14. The local inputs 42 may include information entered by the operator of the local operator workstation 14, such as mouse movement, keyboard entries, instructions, or other similar data.

Similar to the local inputs 42, filtered inputs 44 may be received from the remote operator workstation 16. The filtered inputs 44 may be remote inputs 46 that are entered by the operator at the remote operator workstation 16. The remote operator workstation 16 transmits the remote inputs 46 in the form of remote user inputs 48 to an input guard 50 in the medical facility 12 via the network 20. The input guard 50 may be utilized to restrict or block specific actions by the remote operator workstation 16. For instance, the input guard 50 may prevent the remote operator from activating the imaging system 10. From the input guard 50, filtered inputs 44 may be received at the local operator workstation 14, which may be remote user inputs 48 that are permitted by the input guard 50.

As another source of inputs into the local operator workstation 14, network updates 52 are provided to the local operator workstation 14 from a local network sensor 54 and/or a remote network sensor 56. The network updates 52 may include network information, such as network performance, latency, bandwidth, or network congestion, or similar information. The local network sensor 54 and the remote network sensor 56 may monitor and/or measure the network 20 to determine network performance between the local operator workstation 14 and the remote operator workstation 16. The network updates 52 may be provided to the local operator workstation 14 when the performance of the network changes, intermittently, or based on a specific time interval, for example. The network sensors 54 and 56 may be stand-alone modules coupled to the workstations 14 and 16, one or more routines executed on the workstations 14 and 16, or circuitry in the communication path between the workstations 14 and 16. For instance, the network sensors 54 and 56 may be modules of the workstations 14 and 16 that are in the communication path between the local operator workstation 14 and the remote operator workstation 16.

The network sensors 54 and 56 may exchange handshakes or packets, such as one or more test packets 58 and response packets 60, to measure the amount of time for a packet to traverse the network 20. The packets 58 and 60 may be ping packets or remote framebuffer (RFB) packets, for instance. The packets 58 and 60 may also be a statistically significant size to insure a reasonably accurate measurement of the network latency, which is based on the size of the screen updates 38.

To determine the network performance, the local network sensor 54 may transmit the test packet 58 to the remote network sensor 56 via the network 20. In response to the test packet 58, the remote network sensor 56 may send the response 60 to the local network sensor 54 via the network 20. From the packets 58 and 60, the local network sensor 54 may determine and measure the network performance. With the network performance information, the local network sensor 54 or remote network sensor 56 may compare the network performance with a threshold or predetermined quality of service level. The predetermined quality of service level may be a predefined value that is associated with the network latency and bandwidth availability. If the network performance exceeds the quality of service, then the network sensors 54 and 56 may include that information in the network updates 52.

With the network performance information, the network sensors 54 and 56 may provide the local operator workstation 14 with performance information that may impact the screen updates 38. For instance, the local operator workstation 14 may utilize the network updates 52 to provide an indication to the operator of the local operator workstation 14 of the network performance, which is discussed below. Also, the network updates 52 may be incorporated into the screen updates 38 along with the image data 40, local inputs 42, and filtered inputs 44.

The local operator workstation 14 may utilize these inputs to display the image data to the operator and provide screen update data to the remote operator workstation 16. For instance, the image data 40, local inputs 42, filtered inputs 44, and the network updates 52 may be combined by the local operator workstation 14 to present the operator of the local operator workstation 14 with anatomical features of the patient along with information relating to the imaging system 10, the patient, and the network 20. The local operator workstation 14 may generate screen updates 38 that are to be transmitted to the remote operator workstation 16.

The screen updates 38 may be transmitted to an output guard 62, which may be utilized to block specific portions of the encoded data that is being transmitted to the remote operator workstation 16. As discussed above with the input guard 50, the output guard 62 may prevent the remote operator at the remote operator workstation 16 from accessing specific data or viewing specific regions of the image. The output guard 62 generates a filtered output 64 that includes information that the remote operator is permitted to view at the remote operator workstation 16. The filtered outputs 64 are transmitted to the scanner module 66.

To compensate for the network performance, the filtered outputs 64 may be transmitted to scanner module 66, which may modify the filtered outputs 64 based on network performance. The scanner module 66 may be one or more routines that are within the local operator workstation 14 or a module coupled to the local operator workstation 14. The scanner module 66 may adjust the scanning rate based on the network updates 52 or information related to the network performance within the filtered outputs 64. The scanner module 66 may include a frame buffer scanning algorithm, which is utilized to modify the scanning rate on the local operator workstation 14 or the imaging system 10. By adjusting the scanning rate, the scanner module 66 may capture fewer frames per second when the network 20 is congested. Then, the scanner module 66 may process the filtered outputs 64 to compute the areas of change between the filtered outputs 64. Beneficially, by utilizing the network updates 52 to adjust the scanning rate, the operator at the local operator workstation 14 does not have to manually change the setting to adjust for network congestion. As such, the local operator does not have to restart the local operator workstation 14 or the imaging system 10 to change any static settings. The changes between the filtered outputs 64 may be the scanned outputs 68 that are transmitted to the encoder module 68.

As another compensation for the network performance, the encoder module 70 may encode the scanned outputs 68 received from the scanner module 66 to compress the scanned outputs 68 based on the network performance. The encoder module 70 may utilize different compression or data transmission algorithms to reduce the size of the packets being sent to the remote operator workstation 16. The selection of the encoding algorithm may be based on the network updates 52 or information associated with the network performance within the screen updates 38. For instance, the encoder module 70 may encode the data in a format, such as Joint Photographic Experts Group (JPEG), raw encoding, tight encoding, or other custom compression algorithms. Beneficially, by utilizing the network updates 52 to dynamically adjust the encoding format, the operator at the local operator workstation 14 does not have to manually change the encoding setting to adjust for network congestion. For example, if the network performance is acceptable with network congestion or latency being minimal, then the encoder module 70 may transmit raw data over the network 20 to the remote operator workstation 16. However, if the network performance is outside of the quality of service range, the encoder module 70 may compress the image based on a specific compression format to reduce the size of the packet being transmitted to the remote operator workstation 16. The encoder module 70 generates encoded outputs 72 that are transmitted to the remote operator workstation 16 via the network 20.

At the service provider 18, the remote operator workstation 16 receives the encoded outputs 72 from the local operator workstation 14. The encoded outputs 72 are displayed to the remote operator at the remote operator workstation 16. The encoded outputs 72 may include screen information utilized to display information along with detailed images of a patient's anatomy. The information may include an indication of the network performance along with patient information, as discussed below. The remote operator at the remote operator workstation 16 may enter remote inputs 46 that are transmitted to the local operator workstation 14, as discussed above.

Beneficially, by utilizing the network updates 52 to dynamically or automatically adjust the outputs being transmitted to the remote operator workstation 16, the local operator workstation 14 dynamically manages the modifications of compression formats and/or scanning settings, which are used to adjust for network performance. For example, if the network 20 is performing within the predefined quality of service level, then the workstations 14 and 16 may display an indication that the network performance is acceptable. Likewise, the scanner module 66 may not adjust the scanning rate, while the encoder module 70 may pass the raw data through the network 20 to the remote operator workstation 16. However, if the network is performing at a degraded level, which is outside the quality of service level, then the workstations 14 and 16 may display an indication that the network performance is poor. Accordingly, the scanner module 66 may adjust the scanning rate, while the encoder module 68 may adjust the compression algorithm based on the measured network latency and/or bandwidth.

Alternatively, it should be noted that the screen updates 38 may be transmitted from the imaging system 10 to the local operator workstation 14 and the remote operator workstation 16. In this configuration, the imaging system 10 may receive the filtered inputs 44 and network updates 52. In addition, the imaging system 10 may include the scanning module 66 and encoder module 70, which may utilize the network updates 52 to adjust the scanning rate and encoding of the screen updates 38. Accordingly, the remote operator workstation 16 may receive encoded outputs 72 from the imaging system 10. The local operator workstation 14 may receive raw screen data or the encoded outputs 72 from the imaging system 10. Accordingly, in either configuration, the network updates 52 may be utilized to dynamically adjust the screen data being transmitted to the remote operator workstation 16.

Figure 3:
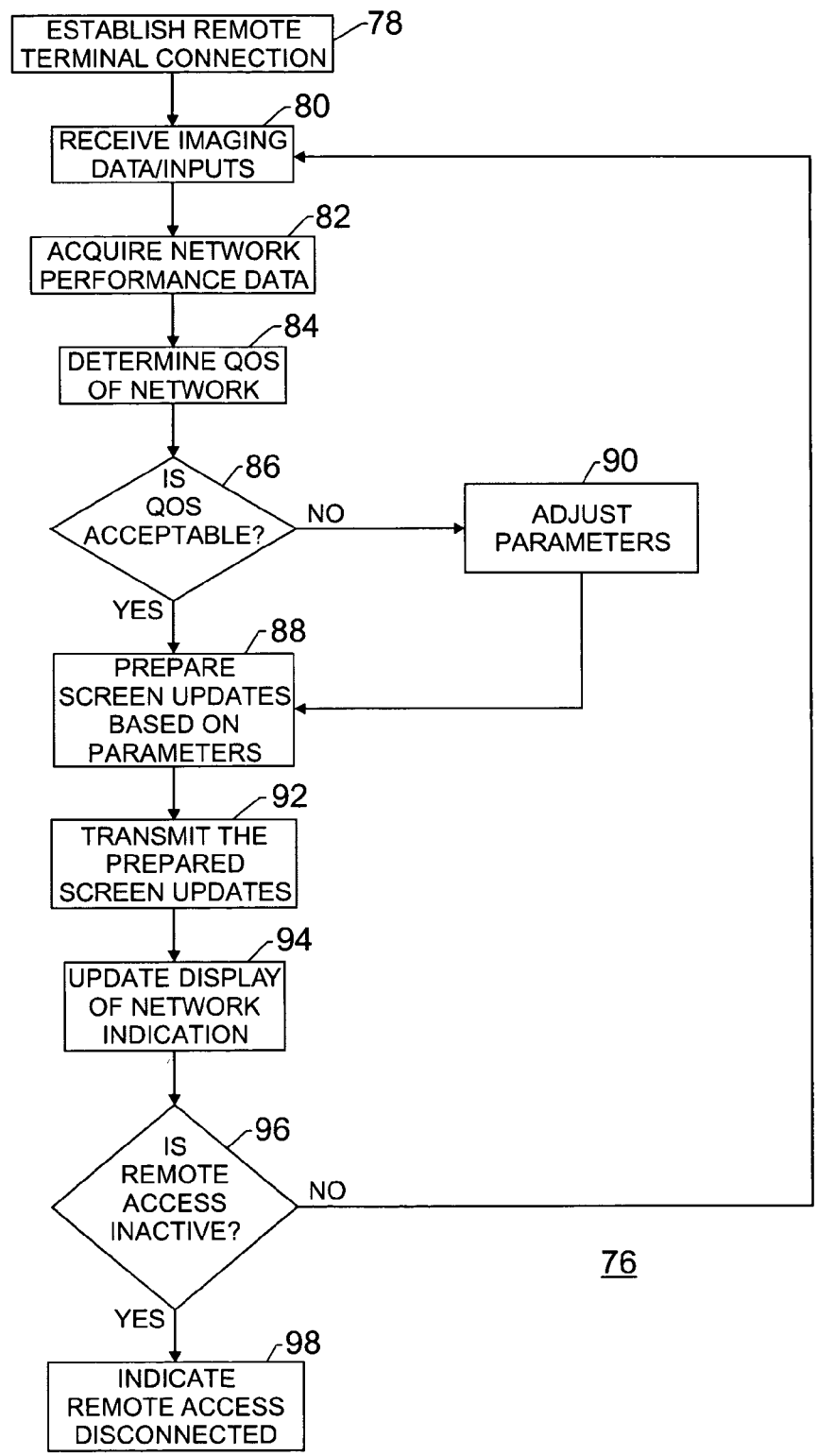
FIG. 3 is a flow chart of exemplary logic for adjusting the screen updates based on the network performance in accordance with the present technique.

To further understand the operation of the remote observation system, FIG. 3 illustrates a flow chart of exemplary logic for adjusting the screen updates based on the network performance. In the flow chart, which is generally referred to by reference numeral 76, the performance of the network, such as network 20 (FIG. 2), is monitored along the communication path between a local operator workstation 14 and a remote operator workstation 16 (FIG. 2). With the measured network performance, the scanner module 66 and/or encoder module 70 (FIG. 2) may be utilized to modify the image updates being transmitted to the remote operator workstation. In addition, the network performance may be communicated to the workstations to provide the operators with an indication of the network performance.

The flow chart 76 begins at block 78 where a connection is established with the remote operator workstation and the local operator workstation. At block 80, the local operator workstation may receive imaging data and inputs from other sources, such as the imaging system 10, the local inputs 42, or remote inputs 46 (FIG. 2), as discussed above. Then, the local operator workstation may acquire network performance data, as shown in block 82. The network performance data may be collected from the network sensors 54 and 56, as discussed above in FIG. 2. The network performance data may update at specified intervals of time or once the network performance has changed a specific amount.

With the imaging data, inputs, and acquired data, the local operator workstation may analyze the network performance to dynamically adjust the image data that is sent to the remote operator workstation. As shown in block 84, the local operator workstation may determine the quality of service (QOS) of the network. The QOS of the network may be based upon defined parameters that relate to an acceptable latency or bandwidth range for the screen updates. The QOS may be broken into different levels that relate to the latency, available bandwidth, or any combination of the network conditions. If the QOS is within a specified range, then the local operator workstation may prepare the screen updates based upon the parameters, as shown in block 88. These parameters may be values or settings stored in memory, which are used to determine the encoding format used in the encoder module 70 and/or the scanning rate in the scanner module 66, as discussed above in FIG. 2. The parameters may be stored within memory of the local operator workstation, the imaging system, the scanner module, and/or encoder module. However, if the QOS is outside the specified range, then the local operator workstation may adjust the parameters, as shown in block 90. The adjustment of the parameters may include changing the encoding format and/or adjusting the scanning rates of the screen updates to comply with another QOS level. Then, the local operator workstation may prepare the screen updates based on the parameters in block 88, as discussed above. Once the encoding and scanning rate adjustments are made, the prepared screen updates may be transmitted to the remote operator workstation, as shown in block 92.

In addition, the local operator workstation may update a network indication that is displayed to the operator, as shown in block 94. The network indication is discussed below in greater detail in FIGS. 4-6. Then, the local operator workstation may determine if the remote operator workstation connection is active or inactive, as shown in block 96. If the remote operator workstation connection is active, then the local operator workstation may acquire additional imaging data and inputs, as discussed above in block 82. However, if the remote operator workstation connection is inactive, then the local operator workstation may indicate that the remote operator workstation has disconnected, as shown in block 98.

Figure 4:
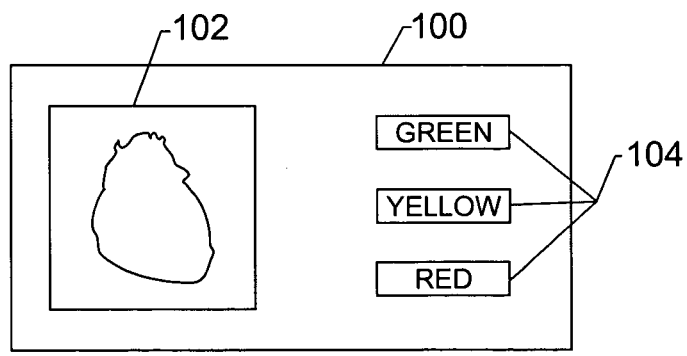
FIG. 4 is an exemplary screen with a network indication for use in accordance with the present technique.
Figure 5:
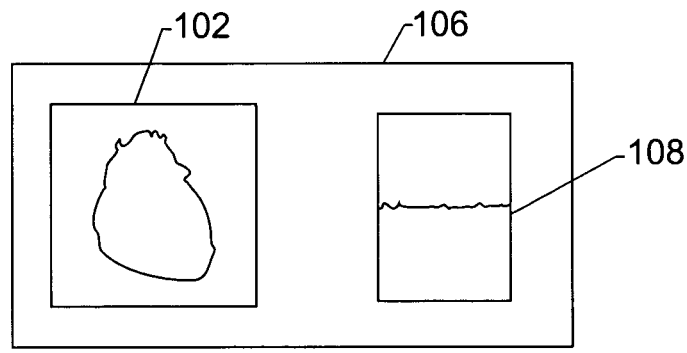
FIG. 5 is an exemplary screen with an alternative network indication for use in accordance with the present technique.
Figure 6:
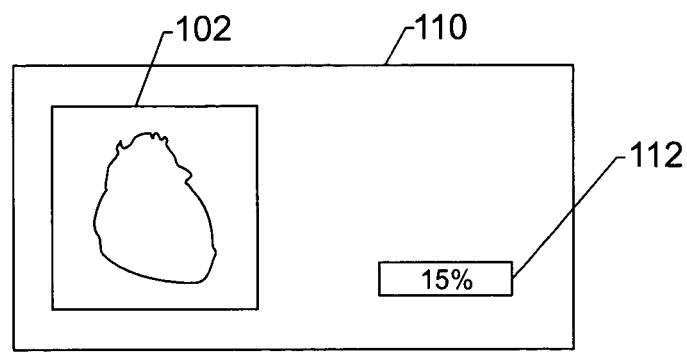
FIG. 6 is an exemplary screen with a second alternative network indication for use in accordance with the present technique.

The indication of the network performance may be displayed to the operator of the local operator workstation 14 or the remote operator workstation 16, as shown in FIGS. 4-6. In FIG. 4, the operator may view an exemplary screen 100 that is displayed on a workstation, such as the local operator workstation 14 and/or remote operator workstation 16 (FIG. 2). The screen 100 may include an image data region 102 and a network indication 104. The image data region 102 may be a view of a patient's anatomy or another image generated from the imaging system. The network indication 104 may include one or more indicators that are used to display the quality of service of the network. For instance, the network indication 104 may be "green," "yellow," or "red." With the indication 104 being "green," the network may be performing with little congestion or minimal latency. If the network indication 104 is "yellow," then the network may be operating with moderate amounts of congestion or the latency may be sporadic with some packets being delayed over the network. With the network indication 104 being "red," the network may be experiencing heavy congestion or the latency may be impacting numerous packets. Through the network indication 104, the operator is presented with a notification of the network performance. This allows the operator to be aware of any network problems that may be impacting the remote training session or diagnostic services being conducted.

In FIG. 5, the operator may view an exemplary screen 106 with an alternative network indication 108 in accordance with embodiments of the present invention. The screen 106 may be displayed on a workstation, such as the local operator workstation 14 and/or remote operator workstation 16 (FIG. 2). The screen 106 may include an image data region 102 and a network indication 108. The image data region 102 is similar to the image data region discussed above in FIG. 4. The network indication 108 may include a bar chart that is used to display the quality of service of the network. For instance, the network indication 108 may be used to present the level of the performance. With the network indication 108 being near the bottom of the bar chart, the network may be performing with little congestion or minimal latency. With the network indication 108 being near the top of bar chart, the network may be experiencing heavy congestion or the latency may be impacting the numerous packets. As a result, through the network indication 108, as noted above, the operator is presented with the network performance in a graduated scale.

In FIG. 6, the operator may view an exemplary screen 110 with a second alternative network indication 112 in accordance with embodiments of the present invention. The screen 110 may be displayed on a workstation, such as the local operator workstation 14 and/or remote operator workstation 16 (FIG. 2). The screen 110 may include a network indication 112 along with the image data region 102, which was discussed above in FIG. 4. The network indication 112 may include numerical digits that are used to represent the network performance. For instance, if the network indication 112 is a low number, such as "10," the network may be performing with little congestion or minimal latency. However, if the network indication 112 is a high number, such as "80," the network may be experiencing heavy congestion or latency, which may impact the remote observation. As a result, the network indication 112 may provide the operator with the network performance in a graduated scale that is easy to understand.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A remote viewing system, comprising:
   a serving station coupled to a medical diagnostic imaging system for controlling the imaging system and configured to receive image data, the serving station comprising:
      a scanner module configured to modify a scanning rate of the image data; and
      an encoder module configured to modify an encoding format of the image data;
   a served station from which a remote operator may interact with the serving station, the served station being configured to receive modified image data from the serving station via a network; and
   a plurality of network sensors in communication with the serving station and configured to provide network performance data to the serving station, wherein the serving station dynamically modifies at least one of the scanning rate and the encoding format based on the network performance data.

2. The remote viewing system of claim 1, wherein the serving station comprises a monitor for presenting image data to an operator.

3. The remote viewing system of claim 2, wherein the serving station is configured to present an indication associated with the network performance data to the operator.

4. The remote viewing system of claim 3, wherein the indication comprises a bar chart.

5. The remote viewing system of claim 3, wherein the indication comprises a network indicator that relates to the network performance data.

6. The remote viewing system of claim 1, wherein the serving station is in communication with an imaging system configured to detect a plurality of signals that are convertible into an image, the imaging system configured to produce the image data.

7. The remote viewing system of claim 1, wherein the plurality of network sensors exchange a plurality of packets to determine network congestion.

8. The remote viewing system of claim 1, wherein the plurality of network sensors exchange a plurality of packets to determine network latency.

9. The remote viewing system of claim 1, wherein the network comprises a wide area network.

10. The remote viewing system of claim 1, wherein the network comprises an Internet.

11. The remote viewing system of claim 1, wherein the serving station receives image data from a medical imaging system.

12. The remote viewing system of claim 1, wherein the serving station utilizes a remote framebuffer protocol to transmit the modified image data to the served station.

13. The remote viewing system of claim 1, wherein the served station transmits remote input data to the serving station.

14. The remote viewing system of claim 1, wherein the serving station receives local input data from a local operator via an input device that is coupled to the serving station.

15. A method for adapting screen updates based on network congestion, the method comprising:
   linking a serving station to a served station via a network, the serving station being coupled to a medical diagnostic imaging system for controlling the imaging system and being configured to receive image data, the served station enabling a remote operator to interact with the serving station, the served station being configured to receive modified image data from the serving station via a network, wherein the serving station utilizes a remote framebuffer protocol to transmit the modified image data to the served station;
   measuring network performance between a serving station and a served station, wherein the serving station provides screen data derived from an imaging system to the served station; and
   adjusting the screen data transmitted to the served station automatically based on the measurement of the network performance, wherein adjusting the screen data comprises modifying a frame buffer scanning algorithm based on the network performance.

16. The method of claim 15, wherein measuring network performance comprises transmitting a test packet from the serving station and receiving a response packet from the served station.

17. The method of claim 15, comprising converting image data from the imaging system into screen data.

18. The method of claim 15, wherein the imaging system comprises one of a computed tomography imaging system, an magnetic resonance imaging system, a tomosynthesis system, a positron emission tomography imaging system, and a X-ray imaging system.

19. The method of claim 15, comprising transmitting the screen data to the served station from the serving station.

20. The method of claim 15, comprising encoding the screen data for transmission to the server station.

21. The method of claim 20, wherein adjusting comprises modifying a data transmission algorithm that compresses the screen data based on the network performance.

22. The method of claim 15, comprising displaying an indication of the network performance at one of the serving station and the served station based on the measurement of the network performance.

23. A method for adapting screen updates based on network performance, the method comprising:
 linking a serving station to a served station via a network, the serving station being coupled to a medical diagnostic imaging system for controlling the imaging system and being configured to receive image data, the served station enabling a remote operator to interact with the serving station, the served station being configured to receive modified image data from the serving station via a network;
 detecting network performance between a serving station and a served station;
 comparing the network performance to a specified range; and
 modifying a plurality of screen updates dynamically based upon the comparison of the network performance.

24. The method of claim 23, wherein the network performance corresponds to the latency of a network coupling the serving station and the served station.

25. The method of claim 23, wherein dynamically modifying the plurality of screen updates comprises adjusting a frame buffer scanning algorithm based on the network performance.

26. The method of claim 23, wherein dynamically modifying the plurality of screen updates comprises adjusting an encoding algorithm based on the network performance.

27. The method of claim 23, comprising encoding the plurality of screen updates for transmission to the served station.

28. A system for adapting screen updates based on network performance, the system comprising:
 a serving station coupled to a medical diagnostic imaging system for controlling the imaging system and configured to receive image data;
 a served station from which a remote operator may interact with the serving station, the served station being configured to receive modified image data from the serving station via a network;
 means for detecting network performance between the serving station and the served station;
 means for comparing the network performance to a specified range; and
 means for dynamically modifying a plurality of screen updates based upon the comparison of the network performance to the specified range.

29. A system for adapting screen updates based on network congestion, the system comprising:
 a serving station coupled to a medical diagnostic imaging system for controlling the imaging system and configured to receive image data, wherein the serving station receives local input data from a local operator via an input device that is coupled to the serving station;
 a served station from which a remote operator may interact with the serving station, the served station being configured to receive modified image data from the serving station via a network;
 means for measuring network performance between the serving station and the served station, wherein the serving station provides screen data derived from an imaging system to the served station; and
 means for automatically adjusting the screen data transmitted to the served station based on the measurement of the network performance, wherein adjusting the screen data comprises modifying a frame buffer scanning algorithm based on the network performance.

30. A remote viewing system for a medical imaging system, comprising:
 an imaging system configured to detect a plurality of signals that are convertible into an image, the system configured to produce image data;
 a serving station configured to receive the image data and control the imaging system, the serving station comprising:
  a scanner module configured to modify a scanning rate of the image data; and
  an encoder module configured to modify an encoding format of the image data;
 a served station configured to receive modified image data from the serving station and to interact with the serving station via a network; and
 a plurality of network sensors in communication with the serving station and configured to provide network performance data to the serving station, wherein the serving station dynamically modifies at least one of the scanning rate and the encoding format based on the network performance data.

31. The remote viewing system of claim 30, wherein the imaging system comprises one of a computed tomography imaging system, an magnetic resonance imaging system, a tomosynthesis system, a positron emission tomography imaging system, and a X-ray imaging system.

32. The remote viewing system of claim 30, wherein the serving station is configured to present an indication associated with the network performance data to an operator.

33. The remote viewing system of claim 30, wherein the plurality of network sensors exchange a plurality of packets to determine network performance.

34. The remote viewing system of claim 30, wherein the network comprises a wide area network.

35. The remote viewing system of claim 30, wherein the plurality of network sensors exchange a plurality of packets to determine network latency.

36. The remote viewing system of claim 30, wherein the serving station utilizes a remote framebuffer protocol to transmit the modified image data in the served station.

37. The remote viewing system of claim 30, wherein the served station transmits remote input data to the serving station.

\* \* \* \* \*